US006995282B1

(12) United States Patent
Fauconet et al.

(10) Patent No.: US 6,995,282 B1
(45) Date of Patent: Feb. 7, 2006

(54) METHOD FOR PURIFYING ACRYLIC ACID OBTAINED BY OXIDATION OF PROPYLENE AND/OR ACROLEIN

(75) Inventors: Michel Fauconet, Valmont (FR); Denis Laurent, Saint-Avold (FR); Mireille Stojanovic, Paris (FR)

(73) Assignee: Arkema, Puteaux (FR)

( * ) Notice: Subject to any disclaimer, the term of this patent is extended or adjusted under 35 U.S.C. 154(b) by 303 days.

(21) Appl. No.: 10/070,999

(22) PCT Filed: Sep. 12, 2000

(86) PCT No.: PCT/FR00/02505

§ 371 (c)(1),
(2), (4) Date: Aug. 6, 2002

(87) PCT Pub. No.: WO01/19769

PCT Pub. Date: Mar. 22, 2001

(30) Foreign Application Priority Data

Sep. 14, 1999 (FR) .................................. 99 11483

(51) Int. Cl.
 *C07C 51/42* (2006.01)
(52) U.S. Cl. ..................................... 562/600
(58) Field of Classification Search ................ 562/600
 See application file for complete search history.

(56) References Cited

U.S. PATENT DOCUMENTS

| 5,780,679 A | 7/1998 | Egly et al. |
| 5,817,865 A | 10/1998 | Machhammer et al. |
| 5,831,124 A | 11/1998 | Machhammer et al. |
| 6,166,248 A | 12/2000 | Heida et al. |
| 6,281,386 B1 * | 8/2001 | Fauconet et al. ........... 562/600 |

FOREIGN PATENT DOCUMENTS

| DE | 19627850 A | | 1/1998 |
| DE | 196 31 628 A1 | | 2/1998 |
| EP | 706986 A | | 4/1996 |
| FR | 2146386 A | | 3/1973 |
| FR | 2756280 A | | 5/1998 |
| WO | WO 98/23573 | * | 6/1998 |

* cited by examiner

*Primary Examiner*—Paul A. Zucker
(74) *Attorney, Agent, or Firm*—Millen White Zelano & Branigan, P.C.

(57) ABSTRACT

The gas reaction mixture (1), formed of propylene, if the case arises, of ultimate oxidation products, of acrylic acid, of acrolein, of steam, of acetic acid and of heavy products, is sent to the bottom of an absorption column (C1) fed countercurrentwise at the top with a heavy hydrophobic absorption solvent. The gas flow (7), formed of propylene and of ultimate oxidation products, of major amounts of water and acetic acid, and of acrolein, is obtained at the top of (C1) and a flow (4), formed of acrylic acid, of the heavy solvent, of heavy products and of minor amounts of acetic acid and of water, is obtained at the bottom of (C1). The flow (7) is sent to a heat exchanger (C3), where it is brought into contact with a descending liquid stream (8), fed at the top of (C3), composed of the recycling of a portion of the flow (9), cooled beforehand, from the bottom of (C3), in order to obtain, at the top, a gas flow (10) comprising the compounds present in the flow (7), except for most of the water and all the acetic acid, removed in the flow (9) from the bottom of (C3).

15 Claims, 1 Drawing Sheet

Single Figure
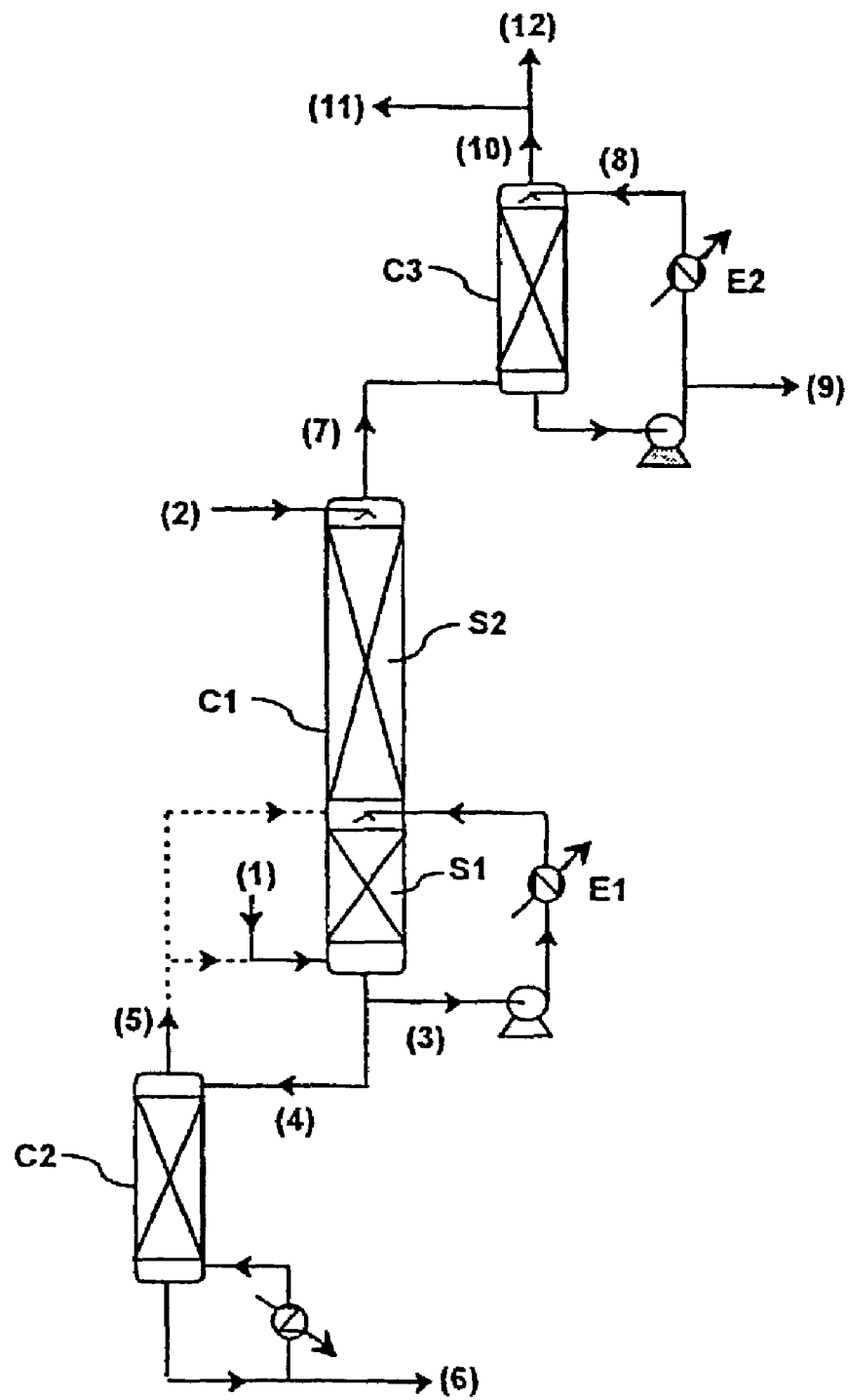

METHOD FOR PURIFYING ACRYLIC ACID OBTAINED BY OXIDATION OF PROPYLENE AND/OR ACROLEIN

The present invention relates to a process for the purification of acrylic acid obtained by oxidation of propylene and/or of acrolein by the catalytic route or by the redox route.

The main process for the catalytic synthesis of acrylic acid uses a reaction for the catalytic oxidation of propylene using a mixture comprising oxygen. This reaction is generally carried out in the vapour phase and generally in two stages:
 the first stage carries out the substantially quantitative oxidation of propylene to a mixture which is rich in acrolein, acrylic acid being a minor component of this mixture;
 the second stage completes the conversion of the acrolein to acrylic acid.

The reaction conditions for these two stages are different and require very precise control of the operating parameters of the reactors.

The reaction can also be carried out in a single reactor but, in this case, it is necessary to separate and recycle large amounts of acrolein to the oxidation stage.

The redox route has been disclosed in French Patent Applications FR-A-2 760 008 and 2 760 009: the first relates to the first stage in the manufacture of acrylic acid, namely the manufacture of acrolein by the oxidation of propylene in the gas phase in the absence of molecular oxygen, by passing the propylene over a solid composition formed of specific mixed oxides, which composition acts as redox system and supplies the oxygen necessary for the reaction; and the second relates to the second stage of the manufacture of acrylic acid, according to which a gaseous mixture of acrolein and of steam and, if appropriate, of an inert gas is passed over a solid composition formed of specific mixed oxides, which acts as redox system and supplies the oxygen necessary for the reaction.

As a general rule, these reactions are carried out in multitubular reactors, the processes being referred to as "with a stationary bed" of catalyst (conventional catalytic route) or "with a stationary bed" of active solid (novel redox route).

A process referred to as the "moving bed" process is also known for each abovementioned stage (manufacture of acrolein from propylene and manufacture of acrylic acid from acrolein), which bed is composed of the abovementioned active solids coated with silica, the reaction being carried out in a reactor of riser type.

The two stated oxidation processes (catalytic and redox) produce the gaseous reaction mixture, a portion of the constituents of which is the same. This mixture is composed
 on the one hand, of compounds which are noncondensable under standard pressure and temperature conditions: unconverted propylene, ultimate oxidation products, such as carbon monoxide and carbon dioxide, or propane or other alkanes optionally present as impurities in the propylene used; and
 on the other hand, of condensable compounds which are liquid at atmospheric pressure and a temperature close to ambient temperature:
  acrylic acid;
  "light" morganic compounds, that is to say with a boiling point lower than that of acrylic acid: water of reaction, unconverted acrolein and compounds resulting from competing oxidation reactions, such as acetic acid, formaldehyde, and the like; and
  "heavy" organic compounds, that is to say with a boiling point greater than that of acrylic acid: maleic anhydride, furfuraldehyde, benzaldehyde, and the like.

In addition to these compounds which are common to both processes, the composition of the gas mixture resulting from the reaction for the oxidation of propylene according to a redox process, characterized by the separation of the stages of the oxidation of propylene or of acrolein and for the reoxidation of the active solid, is significantly different from that of a catalytic process, in which the oxidation of propylene or of acrolein and the reoxidation of the catalyst are carried out simultaneously. Thus, as a result of the separation of the stages for the oxidation of propylene (in the absence of air or in the presence of a small amount of air) and for the regeneration of the active solid by air, the reaction gas from a redox process does not comprise nitrogen, which constitutes the main non-condensable inert compound of the conventional catalytic oxidation process. Consequently, the volume of inert compounds is greatly reduced in the redox reaction.

Furthermore, in contrast to a catalytic process, since total reactive convertion is not targeted in the case of a redox process, the gas mixture comprises a not insignificant amount of unconverted propylene and the concentration of water and of acrolein is greater in the gases emerging from a redox reactor.

As a result of these distinctive features, the profitability of the process requires the quantitative recovery of the unconverted propylene and the unconverted acrolein. On the other hand, the steam has to be partially bled in order to prevent its accumulation in the loop for recycling the gases feeding the reactor.

However, it is always advantageous to achieve these objectives in the case also of a conventional catalytic reaction.

An aim of the present invention is to provide a process for the purification of acrylic acid which makes it possible in particular to selectively and quantitatively recover, from the non-condensed gases from the absorption column top, the unconverted reactants (propylene, acrolein) for the purpose of recycling them to the reaction stage and to separate a sufficient amount of water to prevent its accumulation in the loop composed of the fresh gases introduced into the reactor and the recycled gases.

The purification processes described in literature consist in condensing the gas mixture resulting from the reaction and in extracting the organic compounds by countercurrentwise washing using water or heavy hydrophobic solvents.

French Patent No. 1 558 432 discloses a process which consists in separating acrylic acid from the reaction gases from the oxidation of propylene or of acrolein by countercurrentwise absorption using acid esters which are aliphatic or aromatic with high boiling points, or tributyl or tricresyl phosphate. On conclusion of this absorption stage, the light products (acrolein, formaldehyde) are removed at the top of a first distillation column, and a second distillation column makes it possible to obtain, at the top, an aqueous acrylic acid solution which is more concentrated than in the prior art. The claimed solvents are relatively polar and, consequently, the solution of crude acrylic acid obtained on conclusion of the absorption stage is still rich in water. This does not render the process very attractive, as the subsequent separation of the water still requires expensive operations.

French Patent No. 2 002 126 discloses the use of a mixture of fractions with a high boiling point, recovered at the bottom of the columns for the purification of the esters manufactured from acrylic acid, mainly comprising maleates, poly(acrylic acid)s and polyacrylates. The process makes it possible to remove in a single stage, at the top of a distillation column, most of the compounds with low boiling points, such as acrolein, formaldehyde, water and acetic acid. However, this process for the manufacture of acrylic esters is poorly suited to the production of pure acrylic acid, in particular because of the presence, in the starting crude acrylic acid mixture, of the esterification derivatives recycled to the absorption stage.

French Patent No. 2 146 386 discloses a process for the purification of acrylic acid obtained by absorption using a heavy hydrophobic solvent composed of diphenyl and of diphenyl ether. French Patent No. 2 196 986 discloses a process for the purification of acrylic acid obtained by absorption using a solvent composed of a carboxylic acid ester with a boiling point of greater than 160° C. Diethyl phthalate is mentioned as a solvent example. U.S. Pat. No. 5,426,221 discloses a process for the purification of acrylic acid obtained by absorption using a mixture of heavy hydrophobic solvents composed of diphenyl, diphenyl ether and dimethyl phthalate. These three patents make it possible to obtain, on conclusion of the extraction stage, an anhydrous solution from which has been removed a substantial part of the light organic products of which the initial gas mixture was composed (acrolein, formaldehyde, acetic acid), thus substantially facilitating the subsequent purification of the acrylic acid. They do not disclose the recovery of acrolein and the removal of water from the nonabsorbed gases for the purpose of recycling them to the reaction stage.

In addition, the use of relatively polar solvents of the carboxylic acid esters type exhibits the major disadvantage of promoting the formation of new impurities by a hydrolysis side reaction resulting in the dissociation of the ester into its corresponding carboxylic acid and its corresponding alcohol, it moreover being possible for the latter to react with acrylic acid to generate the acrylic ester of the alcohol in question. Thus, in the presence of water, dimethyl phthalate undergoes a hydrolysis side reaction promoted by the temperature of the absorption stage. This side reaction results in the formation of new impurities, such as phthalic anhydride and methanol, which reacts with acrylic acid to form the corresponding ester (methyl acrylate). The formation of these impurities complicates the subsequent stages of purification of acrylic acid.

French Patent No. 2 287 437 discloses a process for the recovery of acrylic acid in which the acrylic acid present in the reaction gases is absorbed countercurrentwise in a column by a liquid stream, conveyed to the column top, originating from the recycling of a portion of the flow extracted at the bottom of this column. The descending liquid stream is at a temperature below the dew point of the gaseous effluent, without departing from this temperature by more than 15° C. This process makes it possible to separate most of the acrolein by removing it in the gases collected at the column top, while limiting the losses of acrylic acid in these gases. This process is described experimentally in the context of absorption by water. Its major disadvantage is that of generating a very dilute solution of crude acrylic acid in water (2% acrylic acid in water in Example 1), since most of the water is recovered at the column bottom. On this assumption, to obtain pure acrylic acid from these solutions would require a very expensive dehydration treatment. Furthermore, the process disclosed could not be applied in the context of absorption by a heavy solvent without resulting in significant losses of acrylic acid at the top.

European Patent No. 706 986 discloses a process for the recovery of acrylic acid by absorption using a heavy hydrophobic solvent, in which process a section for absorption with water, situated at the top of the column for absorption with the heavy solvent, makes it possible to remove, from the gas flow comprising the nonabsorbed compounds, all the constituents which are condensable at the temperature of the cold water injected (acrolein logically is one of these constituents) and to discharge, in the residual gases, only the inert dilution gases (mainly nitrogen) and the ultimate oxidation gases ($CO$, $CO_2$). The process thus does not disclose the conditions which make possible recycling of the acrolein to the reaction stage.

Surprisingly, the Applicant Company has discovered that, under certain conditions, it is possible to selectively remove most of the water present in the gases resulting from the absorption column and with it the nonabsorbed organic compounds present in these gases, in particular acetic acid, without condensing the unconverted noble reactants (propylene, acrolein), which can thus be easily recycled to the reaction stage. The process according to the invention, by making it possible to recover and to recycle virtually quantitatively the reactants which were not converted during the reaction stage, renders very attractive processes for the oxidation of propylene and/or of acrolein to give acrylic acid, in particular by the redox route, with incomplete conversion of propylene and of acrolein in the absence of oxygen or in the presence of a small amount of oxygen.

Another significant advantage of the process according to the invention results from the fact that, by virtue of the selective removal of water, the noncondensed residual gas is concentrated with regard to its recoverable constituents. For this reason, firstly, the flow recycled to the reaction is more concentrated in propylene and acrolein, which increases the output of the reaction. Secondly, this concentrating effect makes it possible to reduce the flow rate of the bleed flow of the residual gases, necessary in order to prevent the accumulation of the non-condensable ultimate oxidation compounds (carbon monoxide and dioxide), resulting in a reduction in the loss of noble materials. Finally, as the residual gas mixture flow emerging from the absorption column has had most of its water removed, it exhibits a markedly increased calorific value, which makes it possible to destroy it in a steam-producing boiler or to reuse it as fuel, which renders the process more economic in comparison with the existing conventional processes.

The present invention relates to a process for the purification of acrylic acid obtained by oxidation of the propylene and/or acrolein gas substrate by the catalytic route or by the redox route, the said gas mixture resulting from the said reaction being composed mainly of propylene, when the substrate comprises propylene, ultimate oxidation products, acrylic acid, acrolein, steam, acetic acid and heavy products from side reactions, characterized in that:

the reaction gas mixture is sent to the bottom of an absorption column (C1), which column is fed countercurrentwise at the top with at least one heavy hydrophobic absorption solvent, in order to obtain:
at the top of the said column (C1), a gas flow composed of propylene and the ultimate oxidation products of the mixture, major amounts of water and of acetic acid, and acrolein; and at the bottom of the said column (C1), a flow composed of acrylic acid, the heavy absorption solvent or solvents, the heavy products from side reactions, and minor amounts of acetic acid and of water;

the gas flow from the top of the said absorption column (C1) is sent to a heat exchanger (C3), where it is brought into intimate contact with a descending liquid stream, fed at the top of the said heat exchanger (C3), composed of the recycling of a portion of the flow, cooled beforehand, from the bottom of the heat exchanger (C3), in order to obtain, at the top of the heat exchanger (C3), a gas flow comprising the compounds present in the feed flow of the said heat exchanger (C3), except for most of the water and all the acetic acid, which are removed in the flow from the bottom of the heat exchanger (C3).

The reaction gas generally has the following composition (in moles):

3 to 20%, in particular 7 to 10%, of acrylic acid;
10 to 45%, in particular 15 to 30%, of water;
0.1 to 1%, in particular 0.3 to 0.4%, of acetic acid;
0.1 to 6%, in particular 1 to 3%, of acrolein; and
40 to 80%, in particular 50 to 70%, of noncondensable products.

Use is made in particular of one or more heavy hydrophobic absorption solvents having a boiling point at atmospheric pressure of greater than 200° C. In particular, use is made, as heavy hydrophobic absorption solvent, of at least one non-hydrolysable hydrophobic aromatic compound having:

a boiling point at atmospheric pressure of between 260° C. and 380° C., preferably between 270 and 320° C.;
a crystallization temperature of less than 35° C., preferably of less than 0° C.; and
a viscosity of less than 10 mPa.s in a temperature range of 30–80° C.

The hydrophobic aromatic compound or compounds are chosen in particular from those represented by the general formulae (I) or (II):

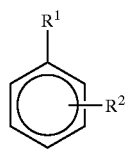

(I)

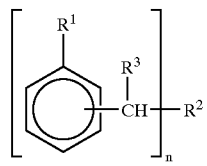

(II)

in which:
$R^1$ represents hydrogen, cycloalkyl or $C_1$–$C_4$ alkyl;
$R^2$ represents cycloalkyl, $C_3$–$C_8$ alkyl, —O—$R^4$ (with $R^4$ representing cycloalkyl or $C_3$–$C_8$ alkyl), —O—Ph($R^5$)-$R^6$ or —Ph—($R^5$)-$R^6$ (with $R^5$ and $R^6$ each independently representing hydrogen or $C_1$–$C_4$ alkyl) (Ph representing a phenyl nucleus);

$R^3$ represents hydrogen or $C_1$–$C_4$ alkyl; and
n has the value 1 or 2;

and those represented by the general formula (III):

(III)

in which:
$R^7$ represents hydrogen or $C_1$–$C_4$ alkyl; and
$R^8$ represents $C_1$–$C_4$ alkyl.

Preferably, ditolyl ether, in the form of a single isomer or of a mixture of isomers, is chosen from this family, which product exhibits the following advantages:

a single constituent (no problem of separation by distillation);
separations of the light products (mainly acetic acid) in the absorption-stripping stage and of the heavy products in the following columns which are rendered easier;
the very low freezing point (−54° C.), which prevents any problem of crystallization in cold weather.

The absorption column (C1) can be fed with one or more pure solvents and/or with one or more solvents originating from a recycling of one or more flows obtained in subsequent purification stages.

In accordance with various specific embodiments of the present invention:

use is made of an absorption column (C1) comprising:
in its lower part, at least one cooling section (S1) equipped with a system for recirculating, through an external exchanger (E1), a portion of the flow collected in the lower part of the said section or sections (S1), in order to return it to the top of the said section or sections; and
in its upper part, a section (S2) for absorbing and rectifying the gas mixture;
the absorption is carried out in the column (C1) at atmospheric pressure or at a pressure close to atmospheric pressure and at a temperature for introducing the solvent or solvents of 20 to 100° C.;
the absorption is carried out in the column (C1) in the presence of at least one polymerization inhibitor chosen in particular from phenol derivatives, such as hydroquinone and its derivatives, for example hydroquinone methyl ether, phenothiazine and its derivatives, such as methylene blue, quinones, such as benzoquinone, metal thiocarbamates, such as copper dibutyldithiocarbamate, compounds comprising nitroso groups, such as N-nitrosophenylhydroxylamine, and amines, such as paraphenylenediamine derivatives. The inhibitor or inhibitors can be introduced with the hydrophobic absorption solvent.

In accordance with a specific embodiment of the present invention, the flow resulting from the column (C1) is sent to a distillation column (C2), in which column distillation is carried out, in order to obtain:

at the top, a flow composed of the light impurities, which is returned to the lower part of the absorption column (C1); and
at the bottom, a flow composed of acrylic acid in solution in the absorption solvent or solvents, a low proportion of acetic acid, the heavy products from side reactions, and the polymerization inhibitor or inhibitors.

The distillation is advantageously carried out in the column (C2) at a pressure of $2.66 \times 10^3$ Pa to $3.33 \times 10^4$ Pa (i.e., 20 to 250 mmHg), at a top temperature of 40–90° C. and at a bottom temperature of 60–150° C.

The heat exchanger (C3) is in particular a direct contact condenser or a partial condensation column.

Furthermore, provision is advantageously made for the gas flow obtained at the top of the heat exchanger (C3) to be at least partially recycled to the reaction stage.

The operation can be carried out in the heat exchanger (C3) at atmospheric pressure or at a pressure close to atmospheric pressure and at a top temperature of 30–90° C., preferably of 50 to 80° C. The percentage of removal of the water on the heat exchanger (C3) is in particular from 20 to 80% by weight, especially from 30 to 70% by weight.

BRIEF DESCRIPTION OF THE DRAWINGS

The single FIGURE in the appended drawing represents the diagram of a plant for implementing the process according to the present invention.

This plant comprises an absorption column C1, a distillation column C2 and a partial condensation column C3.

Absorption Column C1

A flow 1 composed of the reaction gas mixture resulting from the oxidation of propylene and of acrolein in the absence of oxygen, mainly composed:

on the one hand, of compounds which are noncondensable under the operating pressure conditions of the column:
  propylene;
  ultimate oxidation products: CO, $CO_2$;
on the other hand, of condensable compounds:
  acrylic acid;
  acrolein;
  steam;
  acetic acid;
  heavier products from side reactions in very low amounts;

is conveyed to the bottom of the absorption column C1.

The absorption column C1 is fed countercurrentwise at the top with a flow 2 composed of a heavy hydrophobic solvent with a boiling point at atmospheric pressure of greater than 200° C.

Preferably, the absorption column C1 comprises:
  in its lower part, one or more cooling sections S1 equipped with a system for recirculating, through an external exchanger E1, a portion (3) of the flow 4 collected in the lower part of S1, in order to return it to the top of this section;
  in its upper part, a section S2 in which the absorption and the rectification of the mixture are carried out.

The feeding of the solvent (2) is carried out above the section S2. The solvent introduced can be a pure product or can originate from a recycling of the flow obtained in the subsequent purification stages.

The column C1 preferably operates at a pressure close to atmospheric pressure.

The flow 4, obtained at the bottom of the column C1, is mainly composed:
  of acrylic acid;
  of the solvent;
  of small amounts of acetic acid and of water; and
  of stabilizers (polymerization inhibitors).

Distillation Column C2

The light impurities present in the flow 4 are advantageously removed therefrom by conveying it to the distillation column C2, in which column these impurities are removed at the top, with a small amount of acrylic acid and of solvent.

The flow 5 thus obtained is returned to the column C1, at a point situated in the lower part of the latter, preferably at the top or the bottom of one of the cooling sections S1.

The flow 6, obtained at the bottom of the column C2, is then composed mainly of:
  acrylic acid, in solution in the solvent;
  a small proportion of acetic acid; and
  heavy impurities, resulting from side reactions, present in very small amounts in the reaction gas flow.

The column C2 advantageously operates under reduced pressure.

Partial Condensation Column C3

The gas flow 7 resulting from the column C1 comprises the nonabsorbed compounds initially present in the reaction gas:
  products which are non-condensable at the operating pressure of the column: propylene, CO, $CO_2$;
  water;
  acrolein;
  acetic acid.

This flow 7 is sent to the bottom of a column C3, where this gas mixture is brought into intimate contact with a flow 8 of a descending liquid stream, fed at the top of the column C3, composed of the recycling of a portion of the flow 9, cooled beforehand with an external exchanger E2, from the bottom of the column C3.

The gas flow 10 from the top of the column C3 comprises the compounds present in the feed (flow 7) of the column C3, except for most of the water and all the acetic acid, which are removed in the flow 9.

Most of the flow 10 is advantageously recycled to the reaction stage (flow 11), in order to convert the noble reactants which it comprises. This flow can be bled slightly (flow 12) in order to prevent the accumulation in the loop thus formed of non-condensable compounds resulting from the ultimate oxidation of propylene: CO, $CO_2$.

The column C3 advantageously operates at a pressure close to atmospheric pressure.

The following examples illustrate the present invention without, however, limiting the scope thereof. In these examples, percentages are by weight, unless otherwise indicated.

The gas mixture used in these examples has a composition faithful to that of a gas mixture which results from a moving catalytic bed oxidation reactor operating under the conditions for the manufacture of acrylic acid from propylene. It is generated by the complete evaporation, in an air gas flow, of a liquid flow composed of the main constituents of the true reaction mixture, namely:
  of acrylic acid;
  of acrolein;
  of acetic acid; and
  of water.

The air also introduced into the evaporator replaces, at identical concentrations, the gas mixture of non-condensable compounds which are characteristic of the true gas mixture exiting from the moving bed oxidation reactor.

The equipment used in carrying out the examples will now be described with reference to the single figure in the appended drawing.

Column C1

The gas mixture thus generated (1) is conveyed, at a temperature of approximately 160° C., to the bottom of an adiabatic column C1, with an internal diameter of 38 mm, filled with a lower cooling section (S1), equipped with a component of Sulzer EX type, and with an upper absorption/distillation section (S2), equipped with ten packing components of Sulzer EX type. The reaction gas (1) is fed at the bottom of the lower cooling section (S1).

The column C1 is fed, at the top of its upper section S2, with a flow 2 composed of a mixture of the various isomers of ditolyl ether, in which 0.5% of hydroquinone methyl ether has been dissolved beforehand as polymerization inhibitor. The temperature for introducing the absorption solvent can be adjusted by means of an exchanger.

The working pressure in the column C1 is atmospheric pressure.

Column 2

The liquid 4 obtained at the bottom of the absorption column C1 is conveyed, by means of a pump, to the upper part of a column C2 with an internal diameter of 38 mm, equipped with five perforated plates supplied with weirs, at the level of its fourth plate counting from the bottom of the column.

The column C2 is equipped, at the bottom, with a thermosiphon boiler and, at the top, with a condenser.

The distillation is carried out in this column C2 at a reduced pressure of $1.87 \times 10^4$ Pa (140 mmHg).

The liquid flow 6, extracted from the bottom of this column C2, constitutes the crude mixture of acrylic acid from which have been removed the light compounds: non-condensable products, water, acrolein, acetic acid (in part).

Column C3

The nonabsorbed gas flow 7 obtained at the top of the column C1 is conveyed to the bottom of a column C3, with a diameter of 38 mm, filled with glass rings with a diameter of 8 mm over a height of 40 cm.

A portion 8 of the condensed liquid flow collected at the bottom of the column C3 is returned to the top of the same column, by means of a pump, through an exchanger E2 which makes it possible to cool the liquid flow 8 to the desired temperature.

The proportion of the flow from the bottom of the column C3 returned to the top of this column is approximately 10 times the flow recovered at the bottom.

The column C3 operates at atmospheric pressure.

EXAMPLE 1

The synthetic gas mixture is obtained by the complete evaporation, in an airflow (430 l/h), of the mixture in equivalent proportions of the compounds in the liquid state.

Its composition is chosen so as to simulate a true gas exiting from a reactor for the oxidation of propylene and of acrolein by the process in which the oxidation stage is carried out in the absence of oxygen over a moving bed catalyst, in which the degree of conversion of propylene would be 60% and that of acrolein 70%.

This mixture is composed:

on the one hand, of the condensable compounds:

| | |
|---|---|
| acrylic acid | 110.7 g/h (38.8%) |
| water | 139.2 g/h (48.7%) |
| acrolein | 31.7 g/h (11.1%) |
| acetic acid | 3.9 g/h (1.4%); | on the other hand, of an airflow (430 Sl/h) representing the sum of the non-condensable compounds present in the true reaction mixture.

This gas mixture 1 is introduced into the column C1 at a temperature of 152° C. At the top of this column C1, ditolyl ether 2 (mixture of the various isomers+0.5% of hydroquinone methyl ether polymerization inhibitor) is added at a flow rate of 1341 g/h and at a temperature of 50° C. The temperature at the column top reaches 64.1° C. and that of the column bottom 92.6° C.

The synthetic gas mixture is obtained by the complete evaporation, in an airflow (430 l/h), of the mixture in equivalent proportions of the compounds in the liquid state.

Its composition is chosen so as to simulate a true gas exiting from a reactor for the oxidation of propylene and of acrolein by the process in which the oxidation stage is carried out in the absence of oxygen over a moving bed catalyst, in which the degree of conversion of propylene will be 60% and that of acrolein 70%.

This mixture is composed:

on the one hand, of the condensable compounds:

| | |
|---|---|
| acrylic acid | 110.7 g/h (38.8%) |
| water | 139.2 g/h (48.7%) |
| acrolein | 31.7 g/h (11.1%) |
| acetic acid | 3.9 g/h (1.4%); | on the other hand, of an airflow (430 Sl/h) representing the sum of the known condensable compounds present in the true reaction mixture.

This gas mixture 1 is introduced into the column C1 at a temperature of 152° C. At the top of this column C1, ditolyl ether 2 (mixture of the various isomers+0.5% of hydroquinone methyl ether polymerization inhibitor) is added at a flow rate of 1341 g/h and at a temperature of 50° C. The temperature at the column top reaches 64.1° C. and that of the column bottom 92.6° C.

The heating power applied to the boiler of the Column 2 is adjusted so as to remove any trace of water in the flow from the bottom of this column. The flow 6 of acrylic acid obtained at the bottom of the column C2 (1497 g/h) comprises:

- 7.36% of acrylic acid;
- 0.15% of acetic acid;
- 0.014% of acrolein; and
- less than 0.01% of water.

1500 g/h are recovered from the flow obtained at the bottom of the column C3, in order to return it at the top of this same column after having cooled it in the exchanger. The temperature of the non-condensed vapours exiting at the top of the column C3 is 45° C. The flow from the bottom of the column C3 (123.5 g/h) comprises:

- 1.74% of acrylic acid;
- 0.89% of acetic acid; and
- 0.99% of acrolein.

Under these conditions:

the degree of recovery of acrylic acid in the flow from the bottom of the column C2, starting from the reaction gases, reaches 99.5%;

the degree of recovery of acrolein at the top of the column C3, for the purpose of recycling it to the reaction stage, is 94.1%; and the degree of removal of water in the flow from the bottom of the latter column is 86%.

EXAMPLE 2

In this example, the reaction gas composition targeted at the outlet of the evaporator is such that it simulates a reaction for the oxidation of propylene and of acrolein carried out according to the process with decoupling of the stages for oxidation (in the absence of oxygen) and of regeneration of the catalyst (in the presence of oxygen), such that the degree of conversion of the propylene is 90% and that of acrolein is 90%.

The gas mixture is then composed:
on the one hand, of the condensable compounds:
  acrylic acid: 116.3 g/h (40.74%);
  water: 151.2 g/h (53.0%);
  acrolein: 13.3 g/h (4.65%);
  acetic acid: 4.6 g/h (1.64%); and
on the other hand, of an airflow (280 Sl/h) representing the sum of the non-condensable compounds present in the true reaction mixture.

This gas mixture is introduced into the column C1 at a temperature of 152° C. It encounters, countercurrentwise, a flow of ditolyl ether (1170 g/h) introduced at the top of the column at a temperature of 70° C. A temperature of 72.7° C. is measured at the top of the column and a temperature of 92.7° C. is measured at the bottom of the column.

A heating power is applied to the boiler of the column C2 such that no more water is present in the flow from the bottom of this column. The flow of crude acrylic acid obtained at the bottom of the column C2 (1285 g/h) comprises:
  8.86% of acrylic acid;
  0.12% of acetic acid;
  0.003% of acrolein; and
  less than 0.01% of water.

1500 g/h are recovered from the flow obtained to the bottom of the column C3, in order to return it to the top of this same column after having cooled it in the exchanger. The temperature of the non-condensed vapours exiting at the top of the column C3 is 44° C. The flow from the bottom of the column C3 (133.3 g/h) comprises:
  2.24% of acrylic acid;
  2.06% of acetic acid; and
  0.11% of acrolein.

Under these conditions:
the degree of recovery of acrylic acid in the flow from the bottom of the column C2, starting from the reaction gases, reaches 97.8%;
the degree of recovery of acrolein in the flow from the top of the column C3, intended to be recycled, is 98.1%; and
the degree of removal of water in the flow from the bottom of the latter column is 84%.

EXAMPLE 3

The experiment described in Example 2 is repeated under the same conditions, apart from the temperature to which the gas mixture resulting from the column C1 is cooled in the column C3.

The degree of recovery of acrolein (portion of acrolein recovered at the top of the column C3 with respect to the acrolein present initially in the reaction gas) and the degree of removal of water (percentage of water removed at the bottom of the column C3 with respect to the water initially present in the reaction gas) have been recorded in the table below for various temperatures measured at the top of the column C3.

TABLE

| Temperature top C3 | 8° C. | 28° C. | 38° C. | 44° C. | 56° C. | 60° C. |
|---|---|---|---|---|---|---|
| % of recovery acrolein | 89.9 | 94.5 | 97.2 | 98.1 | 98.8 | 98.6 |
| % of removal water | 97.2 | 93.3 | 91.7 | 84 | 69.5 | 56.8 |

What is claimed is:

1. A process for the purification of acrylic acid obtained by catalytic or redox oxidation of a propylene and/or acrolein gas substrate, from a gas mixture (1) resulting from said oxidation comprising mainly propylene, when the substrate comprises propylene, ultimate oxidation products, acrylic acid, acrolein, steam, acetic acid and heavy products from side reactions,
wherein:
  the reaction gas mixture (1) is sent to the bottom of an absorption column (C1), which column is fed countercurrentwise at the top with at least one heavy hydrophobic absorption solvent, in order to obtain:
  at the top of said column (C1), a gas flow (7) composed of propylene and ultimate oxidation products of the mixture (1), major amounts of water and of acetic acid, and acrolein; and
  at the bottom of said column (C1), a flow (4) composed of acrylic acid, the heavy absorption solvent, heavy products from side reactions, and minor amounts of acetic acid and of water;
  the gas flow from the top (7) of said absorption column (C1) is sent to a heat exchanger (C3), where it is brought into intimate contact with a descending liquid stream (8), fed at the top of the said heat exchanger (C3), comprising a previously cooled flow (9), recycled from the bottom of the heat exchanger (C3), in order to obtain, at the top of the heat exchanger (C3), a gas flow (10) comprising the compounds present in gas (7) to said heat exchanger (C3), in which most of the water and all the acetic acid are removed in flow (9) from the bottom of the heat exchanger (C3),
  the flow (10) which contains acrolein is at least partially recycled to catalytic or redox oxidation.

2. A process according to claim 1, which at least one heavy hydrophobic absorption solvent having a boiling point at atmospheric pressure of greater than 200° C. is used.

3. The process according to claim 2, wherein the heavy hydrophobic absorption solvent is at least one nonhydrolysable hydrophobic aromatic compound having:
  a boiling point at atmospheric pressure of between 260° C. and 380° C.;
  a crystallization temperature of less than 35° C.; and
  a viscosity of less than 10 mPa.s in a temperature range of 38–80° C.

4. A process according to claim 3, wherein the hydroponic absorption solvent is a hydrophobic aromatic compound having a boiling point of between 270° C. and 320° C.

5. A process according to claim 3, said hydrophobic aromatic compound having a crystallization temperature of less than 0° C.

6. A process according to claim 3, wherein the hydrophobic aromatic compound or compounds is/are represented by the general formulae (I) or (II):

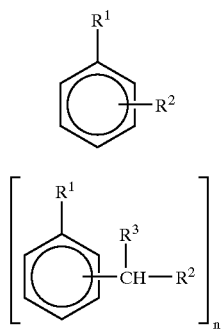

or those represented by the general formula (III):

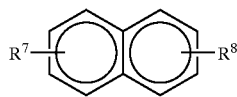

in which:
$R^7$ represents hydrogen or $C_1$–$C_4$ alkyl; and
$R^8$ represented $C_1$–$C_4$ alkyl.

7. A process according to claim 1, characterized in that the absorption column (C1) is fed with one or more pure solvents and/or with one or more solvents originating from a recycling of one or more flows obtained in subsequent purification stages.

8. A process according to claim 1, wherein the absorption column (C1) comprises:
in its lower part, at least one cooling zone (S1) and recirculating, through an external exchanger (E1), a portion (3) of a flow (4) collected in the lower part of the said section or sections (S1), in order to return it to the top of the said section or sections; and
in its upper part, a zone (S2) comprising absorbing and rectifying the gas mixture (1).

9. A process according to claim 1, wherein the absorption is carried out in the column (C1) at atmospheric pressure or at a pressure close to atmospheric pressure and at a temperature for introducing the solvent or solvents of 20 to 100° C.

10. A process according to claim 1, wherein the absorption is carried out in the column (C1) in the presence of at least one polymerization inhibitor.

11. A process according to claim 10, wherein the inhibitor or inhibitors are chosen from phenol derivatives, such as hydroquinone and its derivatives, for example hydroquinone methyl ether, phenothiazine and its derivatives, such as methylene blue, quinones, such as benzoquinone, metal thiocarbamates, such as copper dibutyldithiocarbamate, compounds comprising nitroso groups, such as N-nitrosophenylhydroxylamine, and amines, such as para-phenylenediamine derivatives.

12. A process according to claim 1, a flow (4) resulting from the column (C1) is sent to a distillation column (C2), in which column distillation is carried out, in order to obtain:
at the top, a flow (5) composed of the light impurities, which is returned to the lower part of the absorption column (C1); and
at the bottom, a flow (6) composed of acrylic acid in solution in the absorption solvent or solvents, a low proportion of acetic acid, the heavy products from side reactions, and the polymerization inhibitor or inhibitors.

13. A process according to claim 12, wherein the distillation is carried out in the column (C2) at a pressure of $2.66 \times 10^3$ Pa to $3.33 \times 10^4$ Pa, at a top temperature of 40–90° C. and at a bottom temperature of 60–150° C.

14. A process according to claim 1, wherein the heat exchanger (C3) is a direct contact condenser or a partial condensation column.

15. A process according to claim 1, wherein the heat exchange in the heat exchanger (C3) is concducted at atmospheric pressure or at a pressure close to atmospheric pressure and at a top temperature of 30–90° C., the percentage of removal of the water on the heat exchanger (C3) being from 20 to 80% by weight.

* * * * *

UNITED STATES PATENT AND TRADEMARK OFFICE
CERTIFICATE OF CORRECTION

PATENT NO. : 6,995,282 B1
APPLICATION NO. : 10/070999
DATED : February 7, 2006
INVENTOR(S) : Michel Fauconet et al.

It is certified that error appears in the above-identified patent and that said Letters Patent is hereby corrected as shown below:

Column 12, line 51, reads "claim 1, which" should read -- claim 1, in which --
Column 14, line 16, reads "N-nitros-" should read -- N-nitroso- --
Column 14, line 17, reads "ophenylhydroxylamine" should read
-- phenylhydroxylamine --

Signed and Sealed this

Twenty-ninth Day of August, 2006

JON W. DUDAS
*Director of the United States Patent and Trademark Office*